United States Patent
Hillely et al.

(10) Patent No.: US 8,348,855 B2
(45) Date of Patent: Jan. 8, 2013

(54) MULTIPLE SENSOR DEVICE FOR MEASURING TISSUE TEMPERATURE DURING THERMAL TREATMENT

(75) Inventors: Ron Hillely, Zichron Yaakov (IL); Mordechai Bliweis, Kiryat-Haim (IL)

(73) Assignee: Galil Medical Ltd., Yokneam (IL)

( * ) Notice: Subject to any disclaimer, the term of this patent is extended or adjusted under 35 U.S.C. 154(b) by 1272 days.

(21) Appl. No.: 11/991,167

(22) PCT Filed: Aug. 29, 2006

(86) PCT No.: PCT/IL2006/000999
§ 371 (c)(1),
(2), (4) Date: Feb. 28, 2008

(87) PCT Pub. No.: WO2007/026354
PCT Pub. Date: Mar. 8, 2007

(65) Prior Publication Data
US 2009/0306638 A1      Dec. 10, 2009

Related U.S. Application Data

(60) Provisional application No. 60/711,667, filed on Aug. 29, 2005.

(51) Int. Cl.
*A61B 5/00* (2006.01)
(52) U.S. Cl. .......................................... 600/549; 606/21
(58) Field of Classification Search .................. 600/587, 600/549; 606/50
See application file for complete search history.

(56) References Cited

U.S. PATENT DOCUMENTS

| 3,369,550 | A | | 2/1968 | Armao |
| 3,951,136 | A | | 4/1976 | Wall |
| 4,476,872 | A | * | 10/1984 | Perlin ............................ 600/380 |
| 6,023,638 | A | * | 2/2000 | Swanson ......................... 600/510 |
| 6,197,021 | B1 | * | 3/2001 | Panescu et al. .................. 606/31 |
| 6,428,534 | B1 | * | 8/2002 | Joye et al. ........................ 606/21 |
| 6,514,214 | B2 | * | 2/2003 | Kokate et al. ................. 600/549 |
| 6,875,209 | B2 | | 4/2005 | Zvuloni et al. |
| 2001/0053882 | A1 | * | 12/2001 | Haddock et al. .............. 600/549 |
| 2003/0114843 | A1 | | 6/2003 | Lafontaine |

(Continued)

FOREIGN PATENT DOCUMENTS

DE       4007473       9/1991

(Continued)

OTHER PUBLICATIONS

Communication Relating to the Results of the Partial International Search Dated Nov. 29, 2006 From the International Searching Authority Re.: Application No. PCT/IL2006/000952.

(Continued)

*Primary Examiner* — Max Hindenburg
*Assistant Examiner* — Renee Danega
(74) *Attorney, Agent, or Firm* — Fredrikson & Byron, P.A.

(57) ABSTRACT

The present invention relates to devices and methods for measuring tissue temperature during thermal treatment of a body. More particularly, the present invention relates to a thermal probe comprising a plurality of thermal sensors operable to measure tissue temperatures during thermal treatments such as cryosurgery. Embodiments of the invention enable simultaneous measurements, using a single probe, of temperatures at a plurality of positions within body tissues. A preferred embodiment enables movement of sensors with respect to tissues while the probe is immobilized by being embedded in frozen tissue.

34 Claims, 10 Drawing Sheets

U.S. PATENT DOCUMENTS

| | | | |
|---|---|---|---|
| 2003/0120171 A1 | 6/2003 | Diamantopoulos et al. | |
| 2004/0215294 A1 | 10/2004 | Littrup et al. | |
| 2005/0143723 A1 | 6/2005 | Zvuloni et al. | |
| 2005/0240116 A1* | 10/2005 | Saadat et al. | 600/549 |
| 2006/0079887 A1* | 4/2006 | Buysse et al. | 606/41 |
| 2007/0043342 A1 | 2/2007 | Kleinberger | |

FOREIGN PATENT DOCUMENTS

| | | | |
|---|---|---|---|
| EP | 1281350 | | 2/2003 |
| FR | 2729221 | | 7/1996 |
| GB | 1360353 | | 7/1974 |
| GB | 1427415 | | 3/1976 |
| GB | 2289414 | | 11/1995 |
| JP | 02-114933 | | 4/1990 |
| JP | 2002-107233 | | 4/2002 |
| JP | 2006-153706 | | 6/2006 |
| WO | WO 96/34571 | | 11/1999 |
| WO | WO 03/00686 | * | 7/2002 |
| WO | WO 03/006086 | | 1/2003 |
| WO | WO 2004/071279 | | 8/2004 |
| WO | WO 2007/020641 | | 5/2007 |

OTHER PUBLICATIONS

International Preliminary Report on Patentability Dated Mar. 13, 2008 From the International Bureau of WIPO Re.: Application No. PCT/IL2006/000999.

International Preliminary Report on Patentability Dated Feb. 28, 2008 From the International Bureau of WIPO Re.: Application No. PCT/IL2006/000952.

Official Action Dated Sep. 3, 2008 From the US Patent and Trademark Office Re.: U.S. Appl. No. 11/204,175.

Official Action Dated May 4, 2009 From the US Patent and Trademark Office Re.: U.S. Appl. No. 11/204,175.

Response Dated Jun. 5, 2008 to Official Action of May 5, 2008 From the US Patent and Trademark Office Re.: U.S. Appl. No. 11/204,175.

* cited by examiner

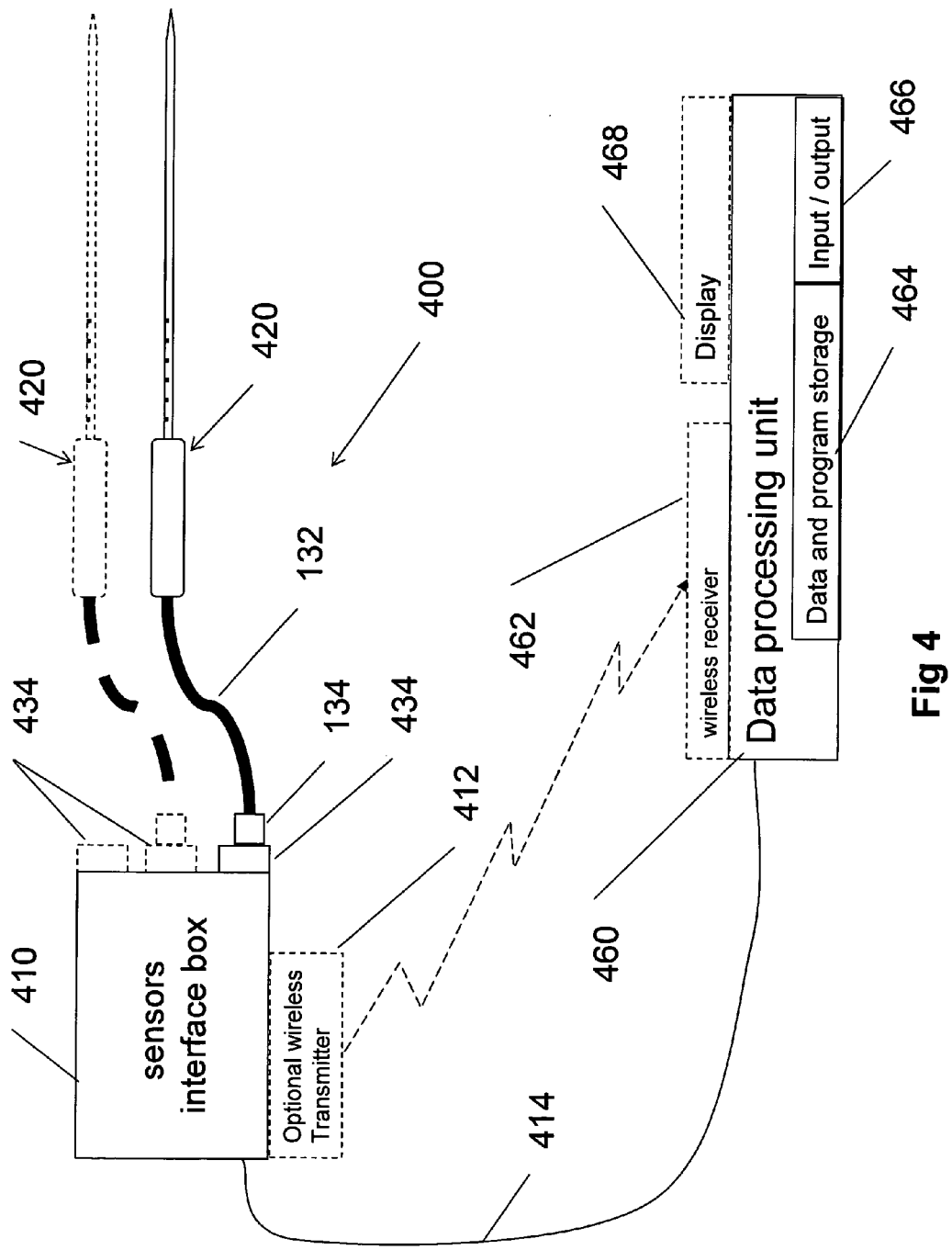

MULTIPLE SENSOR DEVICE FOR MEASURING TISSUE TEMPERATURE DURING THERMAL TREATMENT

RELATED APPLICATIONS

This Application is a National Phase of PCT Patent Application No. PCT/IL2006/000999 having International filing date of Aug. 29, 2006, which claims the benefit of U.S. Provisional Patent Application No. 60/711,667 filed on Aug. 29, 2005. The contents of the above Applications are all incorporated herein by reference.

FIELD AND BACKGROUND OF THE INVENTION

The present invention relates to devices and methods for measuring tissue temperature during thermal treatment of a body. More particularly, the present invention relates to a thermal probe comprising a plurality of thermal sensors operable to measure tissue temperatures during thermal treatments such as cryosurgery. Embodiments of the invention enable simultaneous measurements, using a single probe, of temperatures at a plurality of positions within body tissues. A preferred embodiment enables movement of sensors with respect to tissues while the probe is immobilized by being embedded in frozen tissue.

In thermal ablation, and particularly in cryosurgery, collecting information regarding the three-dimensional thermal profile of tissues in and around a treated organ can be extremely important. Efficiency of thermal treatment procedures is enhanced if thermal data is collected from treated tissues, enabling control systems to supply cooling and/or heating at appropriate times and in appropriate amounts. Safety of thermal treatment procedures is also enhanced by temperature data collection from tissues surrounding ablation targets, such data enabling to control cooling or heating to prevent damage to healthy organs in proximity to a treatment target. Thus, for example, collecting of thermal data from tissues in and around a prostate may facilitate protection of a rectum or a urethra positioned near prostate tissue being ablated.

U.S. Pat. No. 6,142,991 to Schatzberger, entitled "High Resolution Cryosurgical Method And Apparatus", discloses a high resolution cryosurgical method and device for treating a patient's prostate. Schatzberger's method includes the steps of (a) introducing a plurality of cryosurgical probes to the prostate, the probes having a substantially small diameter, the probes being distributed across the prostate, so as to form an outer arrangement of probes adjacent the periphery of the prostate and an inner arrangement of probes adjacent the prostatic urethra; (b) producing an ice-ball at the end of each of said cryosurgical probes, so as to locally freeze a tissue segment of the prostate. The apparatus includes (a) a plurality of cryosurgical probes of small diameter, the probes being for insertion into the patient's organ, the probes being for producing ice-balls for locally freezing selected portions of the organ; (b) a guiding element including a net of apertures for inserting the cryosurgical probes therethrough; and (c) an imaging device for providing a set of images, the images being for providing information on specific planes located at specific depths within the organ, each of said images including a net of marks being correlated to the net of apertures of the guiding element, wherein the marks represent the locations of ice-balls which may be formed by the cryosurgical probes when introduced through said apertures of the guiding element to said distinct depths within the organ. Schatzberger's disclosure includes mention of a single thermal sensor included within a cryoprobe tip, as shown in his FIG. 7. However, the thermal sensor there disclosed is positioned inside the cooling tip of the probe, and therefore is not operable to report temperature of tissues outside the probe during probe operation. U.S. Patent Application No. 2004/0024391 entitled "Apparatus And Method For Protecting Tissues During Cryoablation" by Samuel Cytron et al., filed on Feb. 5, 2004, discloses an apparatus and method for protecting the neurovascular bundle during cryoablation of tissues of the prostate by heating the vicinity of the neurovascular bundle while cooling pathological tissues of a prostate to cryoablation temperatures, thereby cryoablating pathological tissues while protecting the neurovascular bundle from damage. A cryoprobe presented by Cytron also comprises a thermal sensor. Cytron's method for guiding a cryoablation process comprises placing probes containing thermal sensors in intermediate positions around a treated volume.

U.S. Patent Application No. 2005/0143723 entitled "Method For Delimiting Cryoablation By Controlled Cooling", by Roni Zvuloni et al., filed on Jun. 30, 2005, discloses systems and methods for planning a cryoablation procedure and for facilitating a cryoablation procedure, utilizing integrated images displaying, in a common virtual space, a three-dimensional model of a surgical intervention site based on digitized preparatory images of the site from first imaging modalities, simulation images of cryoprobes used according to an operator-planned cryoablation procedure at the site, and real-time images provided by second imaging modalities during cryoablation. The system supplies recommendations for and evaluations of the planned cryoablation procedure, feedback to an operator during cryoablation, and guidance and control signals for operating a cryosurgery tool during cryoablation.

Methods are provided for generating a nearly-uniform cold field among a plurality of cryoprobes, for cryoablating a volume with smooth and well-defined borders, thereby minimizing damage to healthy tissues.

A thermal sensor probe comprising a plurality of thermal sensors is discussed in U.S. Patent Application 2004/0215294 A1 by Littrup et al. In paragraphs 109-114 Littrup discusses a thin probe resistance thermometers (904) constructed in a linear ray along the probe to provide more than two measurement points. Littrup mentions use of a thin outer coating "(e.g. made of TEFLON®)" to "provide for smooth, non-stick insertion of such a probe". Littrup does not teach or suggest that such a coating would enable or facilitate displacement of such a probe within frozen tissues. To the contrary, in the same context in which he presents the TEFLON® coating, Littrup teaches use of heating devices to enable removal or displacement of probes within frozen material.

In other words, Littrup's disclosure does not provide a thermal sensor probe capable of movement within frozen tissue. Once Littrup's probe is incorporated into a body of frozen tissue, the positions of thermal sensors within that probe are fixed with respect to that tissue, and cannot be moved or displaced so long as that tissue is frozen. The immobility of the thermal sensors within such a probe thus severely limit the ability of such a probe to provide detailed and accurate thermal information regarding temperatures at a wide variety of positions within and around the iceball created by a cryoablation procedure.

Moreover, it may be noted that it is advantageous for a thermal sensor probe to be as thin as possible, to facilitate insertion and minimize tissue damage by the probe. Requirements for individual electrical connections to sensors within a probe therefore limit the number of sensors which can be included in a probe while that probe yet remains thin. Therefore, there is an upper limit to the fineness of resolution of thermal readings that can be provided by a thin thermal probe containing a plurality of sensors.

Thus, there is a widely recognized need for, and it would be highly advantageous to have, a thermal sensor probe operable to measure temperatures at a plurality of positions within cooled body tissues. It would be particularly useful to have a sensor or plurality of sensors capable of being freely moved and displaced within frozen tissue, according to informational needs of an operator as those needs vary during various phases of a cryoablation operation, even during times when external walls of that sensor probe are immobilized by adhesion to or pressure from frozen tissues contiguous to that probe. Use of such a probe, or a plurality of such probes, particularly within a context providing accurate positioning information with respect to such thermal probes (e.g. Shatzberger's apparatus discussed above) would enable fine resolution of thermal readings from thin thermal probes within treated tissue, and would thus facilitate accurately delimited cryoablation, automatic control of ablation procedures, and accurate prediction of ablation outcomes based on variably positioned real-time temperature readings during an on-going ablation procedure.

SUMMARY OF THE INVENTION

According to one aspect of the present invention there is provided a thermal sensor probe insertable into body tissue comprising at least one thermal sensor operable to report temperature information dependent on temperature of tissues adjacent to the probe, wherein the thermal sensor is operable to be moveable within the probe while the probe is immobilized with respect to frozen tissue adjacent to the probe.

According to further features in preferred embodiments of the invention described below, the probe comprises a plurality of the thermal sensors, which may be thermocouples or thermistors. Movement of the thermal sensor within the probe may be operable to be controlled manually, or the thermal sensor may be operable to be moved within the probe by a mechanical actuator under algorithmic control. The probe may comprise a position sensor operable to sense and report a position of the thermal sensor within the probe.

According to further features in preferred embodiments of the invention described below, the probe comprises a hollow shaft and a frame, the thermal sensor is mounted on the frame and the frame is moveable within the shaft. A plurality of thermal sensors may be mounted on the frame. The plurality of thermal sensors may be mounted on springy portions of the frame, wherein at least one of the springy portions is so shaped and so positioned that a thermal sensor mounted thereon is pushed into close contact with an external wall of the shaft when the frame is positioned within the shaft.

According to another aspect of the present invention there is provided a thermal sensor probe insertable into body tissue comprising a shaft and a plurality of thermal sensors distributed along the shaft, each of the sensors being so positioned as to be in direct thermal contact with a portion of the shaft.

According to further features in preferred embodiments of the invention described below, the shaft is hollow and each of the plurality of thermal sensors is inserted within the hollow shaft and is directly attached to an external wall of the shaft. At least one of the sensors may be directly attached to the external wall by gluing or by welding. At least one of the thermal sensors may be mounted on an external portion of the shaft and covered by a biocompatible coating.

According to further features in preferred embodiments of the invention described below, the probe comprises a hollow shaft and a frame inserted in the shaft, and at least one of the plurality of thermal sensors is mounted on a spring attached to the frame and held with pressure against an external wall of the shaft when the frame is inserted in the shaft. Preferably, each of the plurality of thermal sensors is mounted on a spring attached to the frame and held with pressure against an external wall of the shaft when the frame is inserted in the shaft. The sensors may be thermocouples or thermistors.

Preferably, the probe comprises a hollow shaft at least a portion of which is designed for insertion into a body, and the plurality of sensors are positioned within the shaft each in direct contact with an interior portion of an external wall of the hollow shaft, and the sensors are so positioned that a minimum distance between one and another of the plurality of sensors is at least an order of magnitude greater than a maximum thickness of the external wall of the insertable portion of the hollow shaft.

Preferably, the probe further comprises a first electronic element operable to receive and process a first signal from one of the thermal sensors and a second electronic element operable to transmit a second signal to a remote data processing unit. The second electronic element may be a wireless transmitter. The first and second electronic elements may be positioned in a handle of the probe, which may also comprise a battery.

According to another aspect of the present invention there is provided a thermal sensor probe insertable into body tissue comprising a hollow shaft and at least one thermal sensor, wherein the thermal sensor is mounted on a spring attached to a frame and is pushed against an external wall of the shaft when the frame is inserted in the shaft. Preferably, the probe comprises a plurality of the thermal sensors mounted on a plurality of springs attached to the frame. The thermal sensors may be thermocouples or thermistors. Preferably the frame is operable to be moveable within the shaft when the probe is inserted in a body.

According to further features in preferred embodiments of the invention described below, the probe shaft comprises at least a partial vacuum.

According to further features in preferred embodiments of the invention described below, at least one of the thermal sensors is a thermocouple which comprises two different metals, and one of the metals is comprised in the frame.

According to further features in preferred embodiments of the invention described below, the probe comprises at least one sub-divider serving to restrict movement of gas between a first vicinity of a first of the plurality of thermal sensors and a second vicinity of a second of the plurality of thermal sensors. Preferably, the probe comprises a plurality of sub-dividers each serving to restrict movement of gas from a vicinity of one of the plurality of thermal sensors to a vicinity of another of the plurality of thermal sensors. The sub-divider may comprise a glue-like substance deposited within a hollow shaft of the probe.

According to another aspect of the present invention there is provided a method of constructing a thermal sensor probe, comprising:
 (a) providing a hollow shaft and a metal frame which comprises a plurality of springy elements;
 (b) mounting a plurality of thermal sensors on the frame, each sensor on a one of the springy elements; and
 (c) inserting the frame with the plurality of mounted thermal sensors into the hollow shaft so that at least one of the springy elements presses at least one of the thermal sensors against an exterior wall of the hollow shaft.

According to another aspect of the present invention there is provided a multiple thermal-sensor apparatus comprising:

(a) a plurality of multiple thermal-sensor probes each of which comprises a plurality of thermal sensors;
(b) an interface unit operable to receive signals from the plurality of sensors of the plurality of probes; and
(c) a data processing unit operable to receiving and processing information from the interface unit.

The interface unit may comprise a wireless transmitter and the data processing unit may comprise a wireless receiver. The data processing unit may further comprise a display.

According to another aspect of the present invention there is provided a thermal ablation system comprising:

(a) a plurality of thermal treatment probes;
(b) a thermal control unit operable to control thermal activities of the treatment probes;
(c) a plurality of thermal sensor probes each of which comprises a plurality of thermal sensors;
(d) an interface unit operable to receive signals from the plurality of thermal sensors of the plurality of thermal sensor probes; and
(e) a data processing unit operable to receiving information from the interface unit and further operable to calculate commands based on the received information and further operable to transmit the calculated commands to the thermal control unit, the thermal control unit being operable to control thermal activities of the thermal probes according to the transmitted commands.

Preferably, the data processing unit is further operable to calculate a three-dimensional model of temperature distribution within body tissue based on information received from the interface unit.

According to another aspect of the present invention there is provided a probe insertable into a body which comprises an indicator operable to report whether tissue temperatures of tissues adjacent to the probe are above freezing temperatures.

The present invention successfully addresses the shortcomings of the presently known configurations by providing a thermal sensor probe operable to measure temperatures at a plurality of positions within cooled body tissues, said probe comprising one or more sensors capable of being freely displaced and repositioned with respect to surrounding tissue, according to informational needs of an operator as those needs vary during various phases of a cryoablation operation, even during times when external walls of that sensor probe are immobilized by adhesion to or pressure from frozen tissues contiguous to the probe.

The present invention further successfully addresses the shortcomings of the presently known configurations by providing a convenient method for constructing a thermal sensor probe operable to measure temperatures at a plurality of positions within cooled body tissues.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

Implementation of the method and system of the present invention involves performing or completing selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 4 is a simplified schematic of a multiple thermal sensor apparatus with an interface for communicating with a data processing unit, according to an embodiment of the present invention.

DESCRIPTION OF THE PREFERRED EMBODIMENTS

Figure 1A:
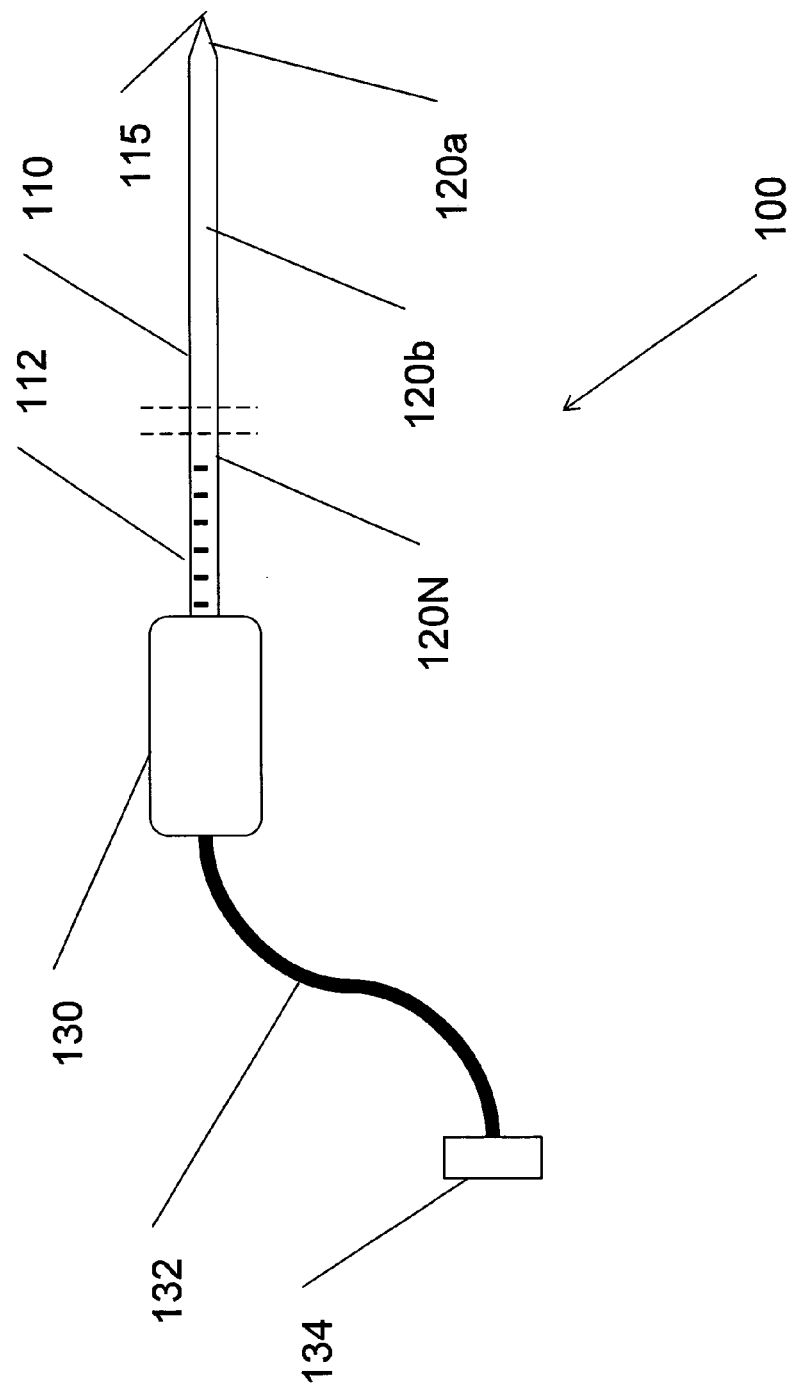
FIG. 1a is a simplified schematic of a multiple thermal-sensor device, according to an embodiment of the present invention.

The present invention is of a multi-sensor thermal probe operable to measure tissue temperatures simultaneously at a plurality of positions. In a preferred embodiment, the probe comprises an elongated frame having a plurality of spring members operable to push thermal sensors against the probe's outer wall. The elongated frame is operable to be displaced within a lumen of the probe, thereby enabling the thermal sensors to be displaced within the probe while the probe is inserted in frozen body tissue, thus enabling taking of tissue temperature readings at a variety of selected thermal sensor positions within and near an iceball while the probe is immobilized in frozen tissue. The probe is thus particularly useful for monitoring cryoablation procedures.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

To enhance clarity of the following descriptions, the following terms and phrases will first be defined:

The term "cryoprobe" is used herein to refer to a therapeutic probe comprising a cooling mechanism. The term "cryosurgical probe" is used herein to refer to a therapeutic probe useful in a cryosurgical context, which probe may or may not comprise a cooling mechanism.

The phrase "heat-exchanging configuration" is used herein to refer to component configurations traditionally known as "heat exchangers", namely configurations of components situated in such a manner as to facilitate the passage of heat from one component to another. Examples of "heat-exchanging configurations" of components include a porous matrix used to facilitate heat exchange between components, a structure integrating a tunnel within a porous matrix, a structure including a coiled conduit within a porous matrix, a structure including a first conduit coiled around a second conduit, a structure including one conduit within another conduit, or any similar structure.

The phrase "Joule-Thomson heat exchanger" as used herein refers, in general, to any device used for cryogenic cooling or for heating, in which a gas is passed from a first region of the device, wherein it is held under higher pressure, to a second region of the device, wherein it is enabled to expand to lower pressure. A Joule-Thomson heat exchanger may be a simple conduit, or it may include an orifice, referred to herein as a "Joule-Thomson orifice", through which gas passes from the first, higher pressure, region of the device to the second, lower pressure, region of the device. A Joule-Thomson heat exchanger may further include a heat-exchanging configuration, for example a heat-exchanging configuration used to cool gasses within a first region of the device, prior to their expansion into a second region of the device.

The phrase "cooling gasses" is used herein to refer to gasses which have the property of becoming colder when passed through a Joule-Thomson heat exchanger. As is well known in the art, when gasses such as argon, nitrogen, air, krypton, $CO_2$, $CF_4$, and xenon, and various other gasses pass from a region of higher pressure to a region of lower pressure in a Joule-Thomson heat exchanger, these gasses cool and may to some extent liquefy, creating a cryogenic pool of liquefied gas. This process cools the Joule-Thomson heat exchanger itself, and also cools any thermally conductive materials in contact therewith. A gas having the property of becoming colder when passing through a Joule-Thomson heat exchanger is referred to as a "cooling gas" in the following.

The phrase "heating gasses" is used herein to refer to gasses which have the property of becoming hotter when passed through a Joule-Thomson heat exchanger. Helium is an example of a gas having this property. When helium passes from a region of higher pressure to a region of lower pressure, it is heated as a result. Thus, passing helium through a Joule-Thomson heat exchanger has the effect of causing the helium to heat, thereby heating the Joule-Thomson heat exchanger itself and also heating any thermally conductive materials in contact therewith. Helium and other gasses having this property are referred to as "heating gasses" in the following.

As used herein, a "Joule Thomson cooler" is a Joule Thomson heat exchanger used for cooling. As used herein, a "Joule Thomson heater" is a Joule Thomson heat exchanger used for heating.

The terms "ablation temperature" and "cryoablation temperature", as used herein, relate to the temperature at which cell functionality and structure are destroyed by cooling. According to current practice temperatures below approximately −40° C. are generally considered to be ablation temperatures.

The terms "freezing temperature" and "freezing temperatures" refer to temperatures at which tissues of a body freeze. Freezing temperature is of course in the vicinity of 0° C., but will vary slightly depending on the exact composition of the tissues being frozen. Temperatures "below freezing temperatures" are of course temperatures below "freezing temperatures."

As used herein, the term "high-pressure" as applied to a gas is used to refer to gas pressures appropriate for Joule-Thomson cooling of cryoprobes. In the case of argon gas, for example, "high-pressure" argon is typically between 3000 psi and 4500 psi, though somewhat higher and lower pressures may sometimes be used.

It is expected that during the life of this patent many relevant thermal sensor probes will be developed, and the scope of the term "thermal sensor probe" is intended to include all such new technologies a priori.

As used herein the term "about" refers to ±10%.

In discussion of the various figures described hereinbelow, like numbers refer to like parts.

The drawings are generally not to scale. Some optional parts were drawn using dashed lines.

For clarity, non-essential elements are omitted from some of the drawings.

Attention is now drawn to FIG. 1a, which represents a simplified schematic of multiple thermal-sensor probe 100, according to an embodiment of the present invention.

Probe 100 comprises a thin needle shaft 110, which is preferably a thin-walled metal tube with circular, oval. rectangular or square cross-section. Shaft 110 preferably has a sharp distal end 115, shaped to facilitate insertion into and penetration of body tissue.

A plurality of thermal sensors 120 (designated 120a, 120b, and 120N in FIG. 1) are positioned within shaft 110. Each of sensors 120 is operable to report information regarding temperatures at its position. Thus, reading that plurality of sensors 120a, 120b, . . . 120N enables garnering temperature information at a plurality of locations along probe 100. In a preferred embodiment, between three and ten sensors 120 are provided. Probe 100 is preferably shaped as a thin needle, to limit damage to tissues caused when probe 100 is inserted into body tissues.

A handle 130 is provided at a proximal end of probe 100, and is useful for holding and manipulating probe 100 during insertion into the tissue. In a preferred embodiment handle 130 contains electrical interface components for transferring signals between thermal sensors 120 and an optional signal cable 132. Signal cable 132 carries electrical signals originating in sensors 120, through an electrical connector 134, to an external unit able to use information contained in those signals. In a preferred embodiment, connector 134 connects to a sensor interface unit 410, described in detail with reference to FIG. 4.

Signal conditioning electronics (such as preamplifiers, electronic noise filtration, analog-to-digital converter (ADC), data multiplexing (MUX), and so on) may be provided in handle 130, in connector 134, in interface unit 410, or at any other convenient position. Signals generated by sensors 120 and/or carried by cable 132 may be in digital format (using either proprietary protocols or standard protocols such as USB or RS232), or else may be conditioned analog signals. Alternatively, no additional electronic components are provided in handle 130 and connector 134, and raw analog signals generated by sensors 120 are presented at connector 134.

Optional markings 112 on shaft 110 can be used as depth guides, enabling insertion of probe 100 to a desired depth within body tissue. Insertion may further be guided by use of a guiding element (not shown), preferably a plate having plurality of apertures such as that taught by Schatzberger, as discussed in the background section hereinabove.

Figure 1B:
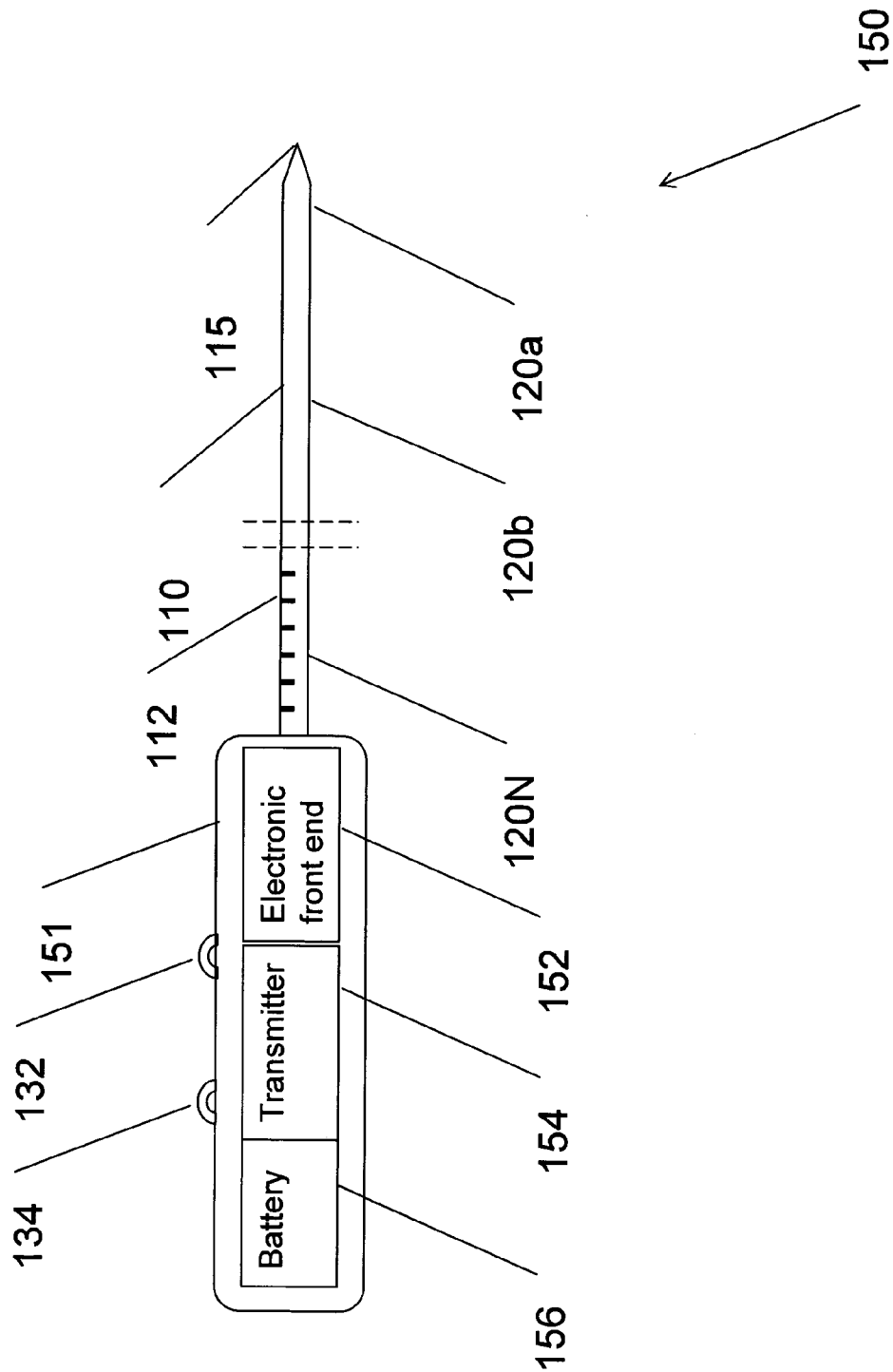
FIG. 1b is a simplified schematic of an alternate configuration of a multiple thermal-sensor device, according to an embodiment of the present invention.

Attention is now drawn to FIG. 1*b*, which is a simplified schematic of a wireless multiple thermal-sensor probe 150, according to a further embodiment of the present invention.

Probe 150 is similar to probe 100 described hereinabove. Probe 150 also comprises a thin (preferably needle-like) shaft 110 having a sharp distal end 115 and a plurality of thermal sensors 120 (marked as 120*a*, 120*b* and 120N in the Figure) positioned along shaft 110 and operable to measure temperatures in their vicinity.

Handle 151 of probe 150 comprises a set of electronic components 152 for receiving and conditioning temperature signals received from probes 120*a*-120N. Electronic components 152 may perform such functions as amplification, noise filtration and other forms of signal conditioning, analog-to-digital conversion, data multiplexing, calibration, etc.

A battery 156 provides power for all electronic components of probe 150.

Probe 150 further comprises a wireless transmitter 154 operable to wirelessly transmit to data processing unit 460 (shown in FIG. 4) data received from sensors 120, which data may optionally be modified en route by electronic components 152. Transmitter 154 may use any wireless transmission method. Thus, transmitter 154 may communicate data using infrared (IR), ultrasonic waves, or RF waves (for example, using the Bluetooth protocol). Digital or analog data formats may be used.

Optionally, two-way communication may be used. For example, data processing unit 460 may transmit data and commands to electronic components 152 of probe 150, communicating, for example, commands to select among alternative modes of operation of probe 150, or commands modifying gain of amplifiers, commands setting temperature sensitivity ranges or other calibration factors, commands modifying sensitivity of temperature readings, commands setting communication protocols or rates of data transmission, commands requesting a reading from specific sensor, commands switching probe 150 to "stand-by" mode to conserve battery power, and so on.

Probe 150 may comprise one or more switches 134 (one shown), used to switch probe 150 on or off, or to manually control its mode of operation.

Probe 150 may further comprise one or more indicators 132 (one shown), preferably embodied s Light Emitting Diodes emitting visible light (LEDs). Indicators 132 are designed and constructed to indicate aspects of status of probe 150, such as/off status, transmission status, low battery warning, device fault, unreadable or dangerous temperatures, etc. Optionally, indicator 132 may be an alphanumerical display. Indicator 132 may be used to indicate which of plurality of sensors 120 is active, or which sensor reading is currently being processed or displayed.

In a particularly useful embodiment, an indicator 132 may indicate whether temperatures the length of probe 150 are above or below freezing temperatures. Since tissues frozen alongside a thermal sensor probe tend to adhere to that probe, an indication that temperatures along probe 150 are above freezing can be used by an operator as a signal that probe 150 can be withdrawn from frozen tissue without risking tissue damaged caused by tissue adherence. Thus, a red LED might be used to indicate temperatures below freezing along at least one portion of probe 150, and a green LED might indicate that probe 150 can be removed easily and without danger to tissues. It is to be noted that the feature described in this paragraph may be incorporated in probes other than thermal-sensor probes, on condition that they include the requisite thermal sensors. In general, probes of various sorts used during cryoablation, including cryoprobes, sensor probes, and other probes, must all await thawing of adjacent tissues (whether by heating of the probe or by natural thawing) prior to withdrawal of the probes from the body. An indicator 132 presenting a visible indication of whether a probe is ready for withdrawal at the end of an operation would consequently be a most useful adjunct to any probe used during cryoablation.

Figure 2A:
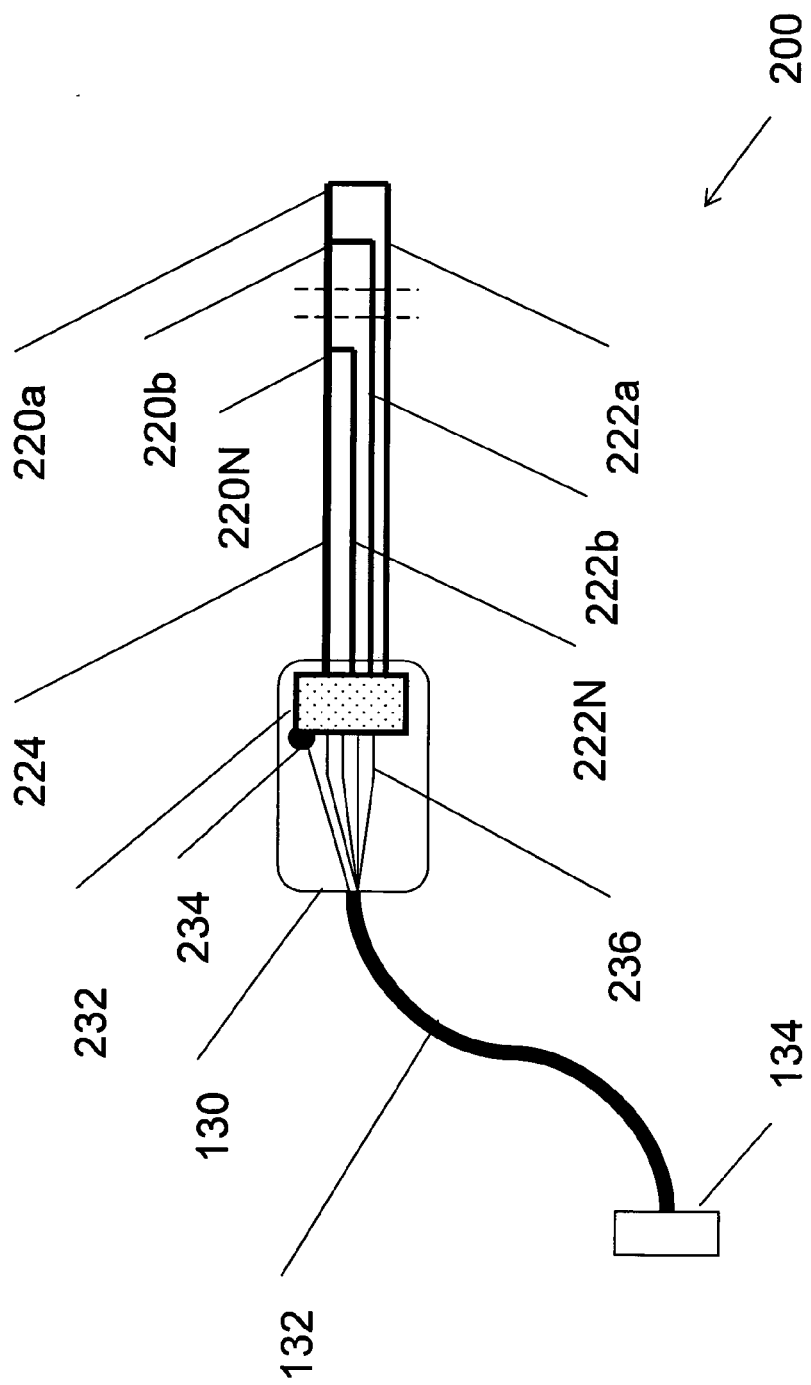
FIG. 2a presents a simplified schematic of construction and wiring details of a multiple thermal-sensor device using thermocouples, according to an embodiment of the present invention.

Attention is now drawn to FIG. 2*a*, which is a simplified schematic of an alternative construction of a multiple thermal-sensor probe using thermocouples, according to an embodiment of the present invention. FIG. 2*a* presents, in particular, electronic connections of a multiple thermal-sensor probe 200 comprising a plurality of thermocouple junctions utilizing a common wire To enhance clarity, probe shaft 110, which is similar to that presented FIGS. 1*a* and 1*b* and discussed above, is not shown in FIG. 2*a*.

FIG. 2*a* presents a plurality of temperature-sensing thermocouple junctions 220, labeled 220*a*, 220*b* and 200N. As is well known in the art, each thermocouple junction 220 is formed as a junction between two types of metal, here designated type A and type B.

In this exemplary embodiment, a common wire 224 is constructed of metal of type A. A plurality of thermocouples 220 are formed at junctions between common wire 224 and a plurality of wires 222, each constructed of metal of type B. Thus, a junction of wire 222*a* with common wire 224 forms thermocouple 220*a*, a junction of wire 222*b* with common wire 224 forms thermocouple 22*b*, and so on.

In a preferred embodiment wires 222 and common wire 224 eventually both connect to copper wires 236 used to connect sensors 220, through cable 132 and connector 134, to electronic devices outside probe 200. Since, if wires of type A and type B are not themselves made of copper, junctions of wires 222 and 224 with copper wire 236 themselves constitute thermocouple junctions, it is recommended that the effects of these latter junctions be controlled or otherwise neutralized. Thus, it recommended that these connections be thermally 'grounded' to a thermal anchor block 232. A thermal sensor 234 may be provided for sensing the temperature of thermal anchor block 232, enabling to calculate electrothermal interactions between wires 222/224 and wires 236, which calculated interactions can be taken into account for calibration of sensors 220 of probe 200. Alternatively or additionally, thermal anchor block 232 may be maintained at a constant, or at a slow changing known temperature. Thermal anchor block 232 may conveniently be housed in handle 130 of probe 200, or in connector 134.

Figure 2B:
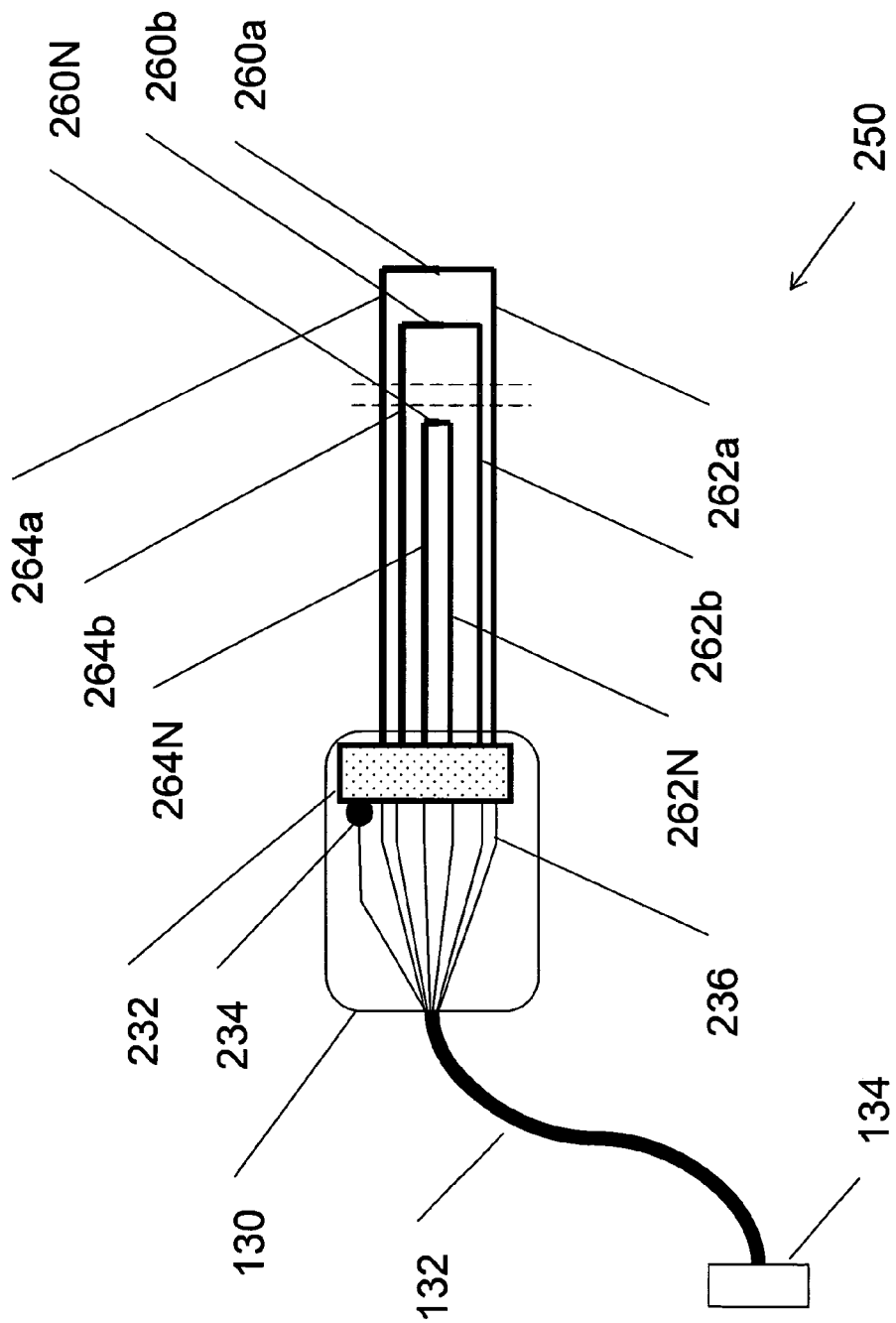
FIG. 2b presents a simplified schematic of construction and wiring details of an alternative configuration of a multiple thermal-sensor device using thermocouples, according to an embodiment of the present invention.

Attention is now drawn to FIG. 2b, which presents an alternative construction of a multiple thermal-sensor probe 250, according to an embodiment of the present invention. In similarity to FIG. 2a, shaft 110 of probe 250, which is similar to that presented above in FIGS. 1a and 1b, is not shown.

Probe 250 is similar to probe 200 in that probe 250 comprises a plurality of thermocouple junctions, but differs from probe 200 in that common wire 224 of probe 200 is not used in probe 250. Instead, separate wires 264, labeled 264a, 264b through 264N, made of metal type A are used. A first thermocouple 260a is formed of a junction between wire 264a made of type A metal and wire 262a made of type B metal. A second thermocouple 260b is formed of a junction between wire 264b made of type A metal and wire 262b made of type B metal. N thermocouples are thus formed at junctions of N wires 264 of type A metal with N wires 262 of type B metal. Other features of probe 250 (e.g. thermal sensor 234, thermal anchor block 232, wires 236, cable 132, connector 134 etc.) are as described hereinabove with respect to FIG. 2a.

Figure 2C:
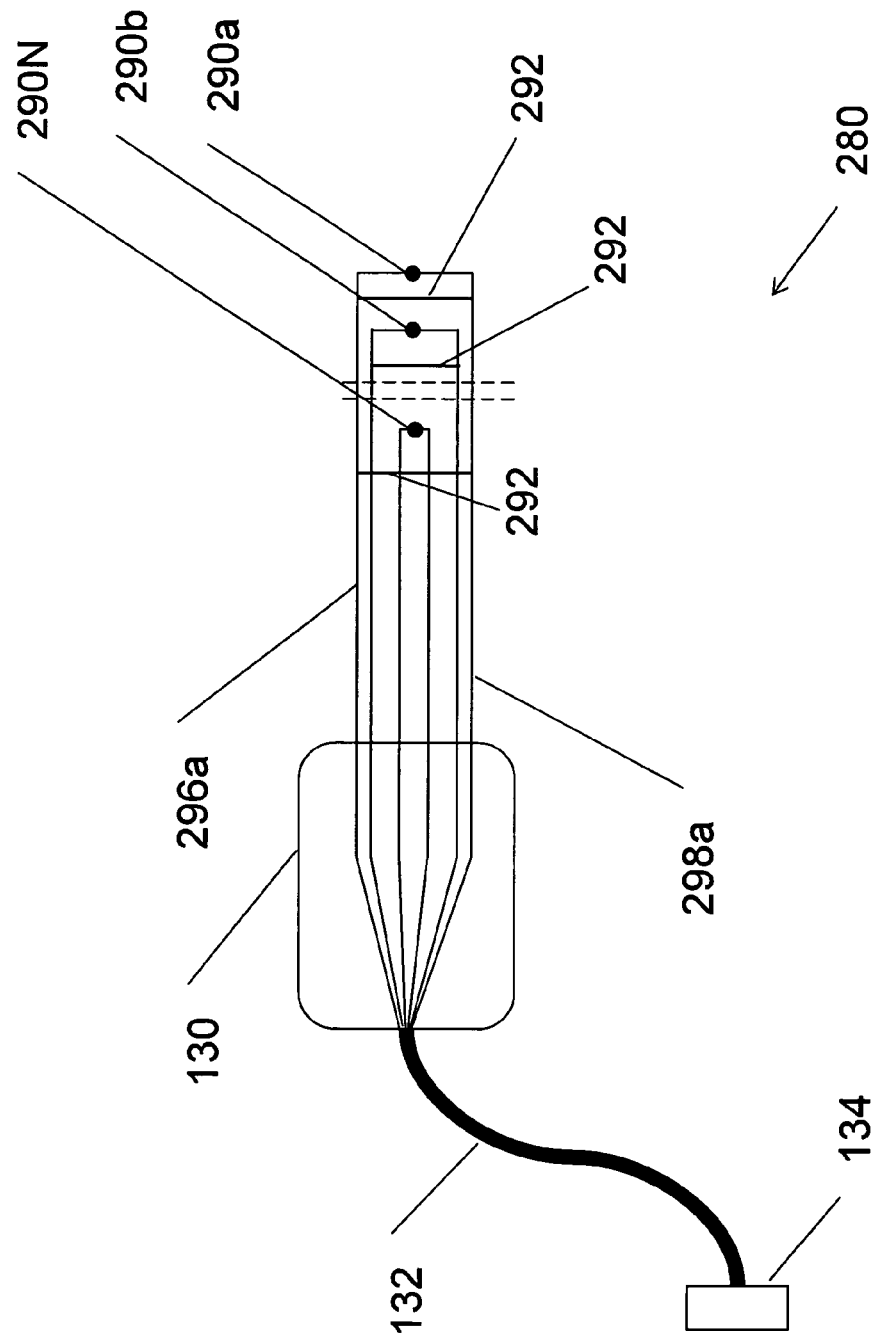
FIG. 2c presents a simplified schematic of construction and wiring details of a multiple thermal sensor device using thermistors, according to an embodiment of the present invention.

Attention is now drawn to FIG. 2c, which presents a simplified schematic of a multiple thermal-sensor probe 280 which comprises thermistors, according to an embodiment of the present invention. In similarity to FIGS. 2a and 2b, internal electrical connections among elements of 280, but not the physical body (shaft) of probe 280, are shown in FIG. 2c.

Probe 280 is similar to probe 250, except that thermistors 290 rather than thermocouple junctions 260 are used to provide temperature-sensitive readouts. Thermistors 290 provide electrical resistance which varies as a function of temperature, hence measurement of voltage drop across a thermistor 290 provides a measure of temperature in a vicinity of thermistor 290.

In an exemplary embodiment shown in FIG. 2c, separate electric wires 296a and 298a are connected to first thermistor 290a. A similar pair of wires provides connection to a second thermistor 290b, and so on, for N thermistors, and all wires 296 and 298 are collected in a cable 132 which terminates in connector 134.

It is noted that features presented with reference to FIGS. 1a-2c may be combined in various combinations within the scope of the current invention. For example, thermocouples including additional metal types may be used to extend the temperature range measurable by the thermocouples or to provide varying degrees of thermocouple sensitivity within a single probe. Different types of thermal sensors (e.g. thermocouples and thermistors) may be used and mixed within a single probe. Distances between sensors may be equal or unequal. Thermal sensors may be concentrated in portions of a probe where high resolution or high accuracy and reliability are desired. A single probe may combine selected features of probes 100, 150, 200, 250 and 280. In particular, thermocouples and thermistors may be combined in a single probe, and common-wire or separate-wire constructions may be utilized with either type of sensor. Embodiments presented in FIGS. 2a-2c may combined with a cable-based handle as presented in FIG. 1a, or a wireless handle as presented in FIG. 1b, and in either case may comprise switches 134 and/or indicators 132.

In a preferred embodiment, the principles of common-wire construction (as exemplified by wire 224 of FIG. 2a) are embodied in such a way that a 'wire' connecting a plurality of sensors or a metal common to a plurality of thermocouple junctions may also serve as a structural member of the device. For example, a probe shaft body 110, or a frame or rod fitting within a lumen of a shaft 110 (such a frame is discussed in detail hereinbelow) may also serve as a metal component of a plurality of thermocouples, or as a common connector to a plurality of thermistors. Use of a structural element of a probe as common element of a plurality of thermocouples or as a common connector to a plurality of thermistors is particularly recommended, as it serves to simplify construction and enhance miniaturization of such thermal probes.

Experiment has shown that thermal sensors which are simply placed inside a thin hollow shaft 110 cannot be relied upon to produce consistent and accurate thermal readings of temperatures of tissues adjacent to shaft 110. Sensors simply placed within a hollow shaft 110 tend to be less sensitive to temperatures of tissue external to shaft 110 than they are to that of air contained within shaft 110, and air currents within shaft 110 cause "cross-talk" between sensors at different positions, as heat is transferred (e.g. by convection currents within the probe) from one position to another. Such crosstalk can be reduced by evacuating shaft 110, but this has the effect of reducing thermal contact between sensors positioned within shaft 110 and tissues external to shaft 110, since without air or another gas to cause convection between sensor and wall, sensors tend to be thermally insulated from adjacent walls and consequently also from those tissues whose temperature it is desired to measure.

Accordingly, air motion inside shaft 110 may be reduced or eliminated by filling or partially filling shaft 110 with an electrically nonconductive jell, or with a glue such as epoxy, which glue may be used both to attach a sensor to an external wall of shaft 110 and to reduce or eliminate air movement and convection currents within shaft 110. Alternatively, air baffles 292 (shown in FIG. 2c) may be introduced inside shaft 110, at least partially separating shaft 110 into separate compartments, preferably each compartment housing no more than one thermal sensor. In a convenient method of construction, baffles 292 may be formed as "Glue balls" large enough to fill or partially fill shaft 110, thereby reducing or preventing air convection currents between sensor regions.

Alternatively or additionally, thermal contact between thermal sensors and tissues, or between thermal sensors and an exterior wall of shaft 110 (which exterior wall is itself in direct contact with body tissues) may be enhanced. In a preferred configuration of probes 100, 150, 200, 250, 280 and other probes described herein, sensors positioned within a hollow shaft 110 are positioned in direct contact with an external wall of shaft 110 in a manner which assures efficient thermal communication between sensors and wall 111, and hence which assures efficient thermal communication (through wall 111) between sensors and tissues exterior to and immediately adjacent to shaft 110. Thus, in a preferred embodiment, thermal contact between thermal sensors and shaft wall is enhanced by attaching sensors to wall 11, preferably by gluing or welding. Also, in preferred embodiments sensors are positioned along shaft 110 at such distances that a minimum distance between one sensor and another is at least an order of magnitude greater than the thickness of wall 111, thus assuring that thermal communication between sensors and tissues, through wall 111 of shaft 110, is more efficient than thermal communication along wall 111 between one sensor position and another.

In a further alternative embodiment, also designed to ensure that thermal communication between sensors and tissues is greater than thermal communication along the length of shaft 110, connecting wires (e.g. 262 and 264 of FIG. 2b, or 296 and 298 of FIG. 2c) are printed on an exterior portion of a wall of shaft 110, and thermal sensors are attached to or printed on that outer wall, which is subsequently coated with bio-compatible material. Sensors are thus brought into close contact with tissues (separated from them only by a coating of bio-compatible material), and may also be thermally isolated from wall 111 of shaft 110, thereby further decreasing cross-talk from one sensor position to another along shaft 110.

Figure 3A:
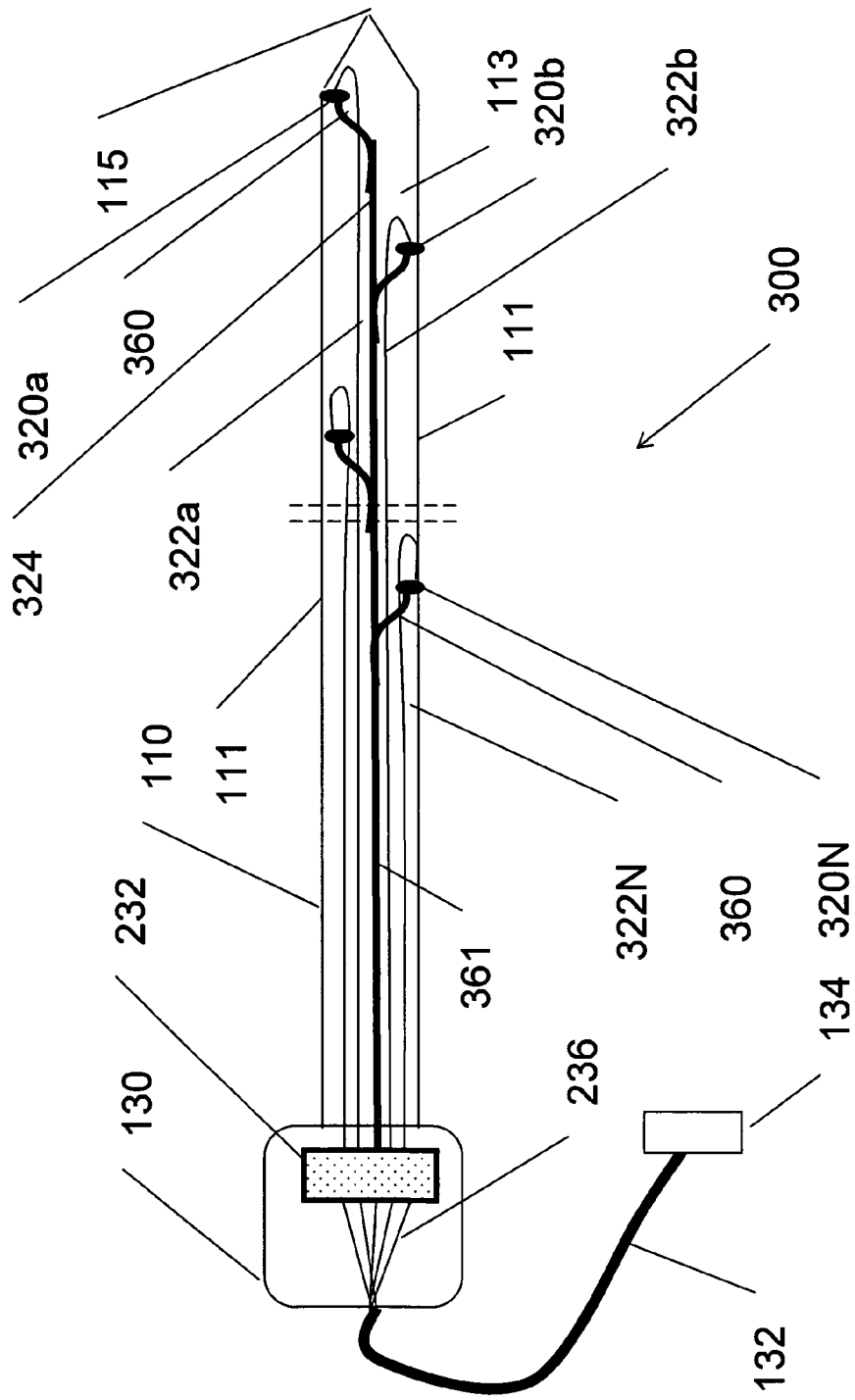
FIGS. 3a and 3b are side and top views respectively of a further alternative construction of a multiple thermal-sensor device, according to an embodiment of the present invention.
Figure 3B:
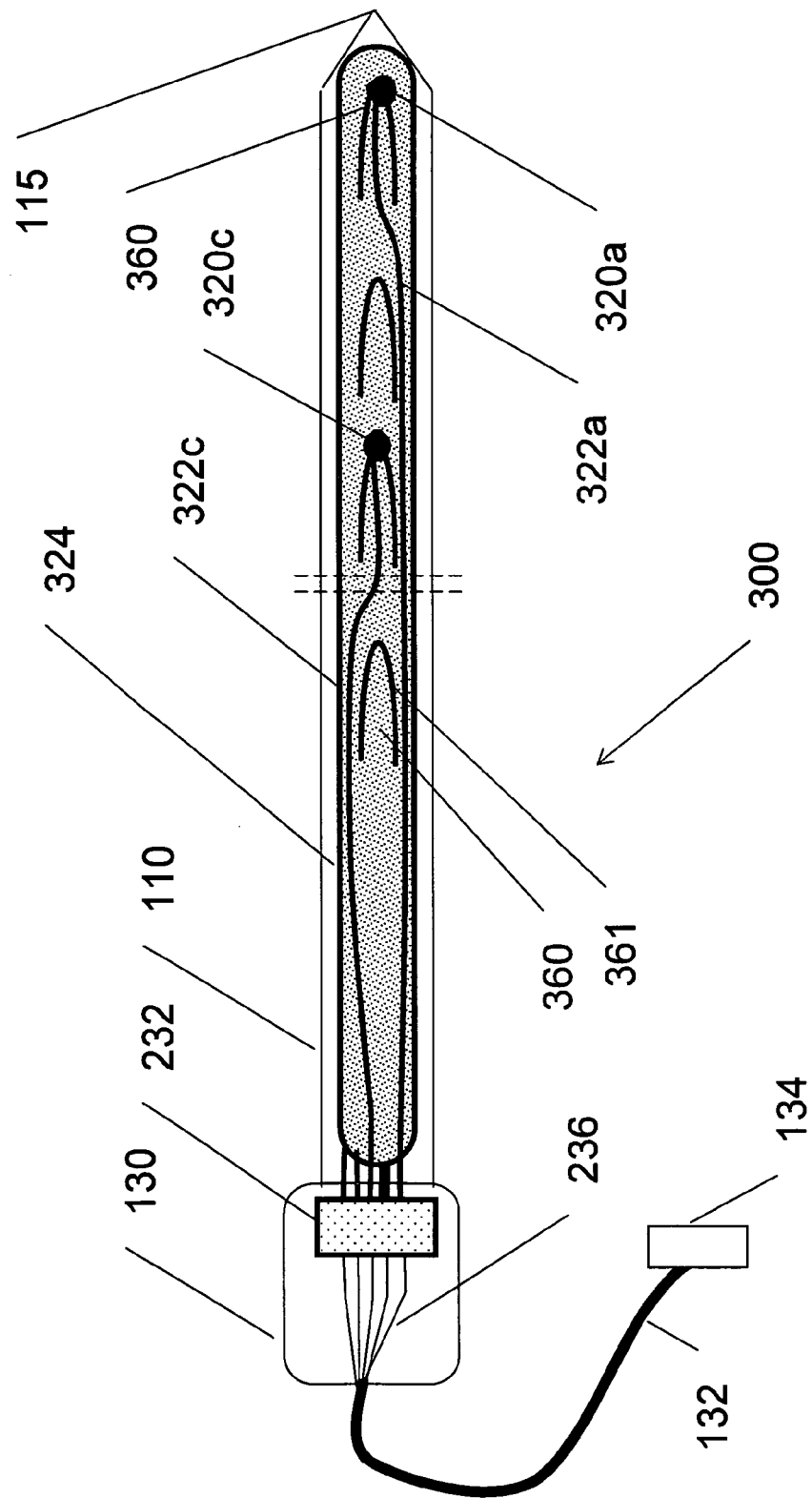

Attention is now drawn to FIGS. 3a and 3b, which present an additional design serving to maximize thermal contact between sensors and tissues through wall 111 of shaft 110. FIGS. 3a and 3b are simplified schematics showing side and top views respectively of a multiple thermal-sensor probe 300 which comprises a spring frame acting as a common connector, according to an embodiment of the present invention.

In similarity to probes presented in FIGS. 1a and 2b, probe 300 comprises a shaft 110 with a sharp distal end 115 designed for penetrating tissue and a handle 130 containing a thermal anchor block 232 and copper wires 236 collected in a cable 132 which terminates at connector 134. A plurality of thermal sensors 320 (preferably thermocouples or thermistors) are provided to give temperature readings at a plurality of positions along the length of probe 300. A thermal sensor 134 (as shown in FIG. 2a) for measuring temperature of thermal anchor block 232 is optional.

As discussed above, it is desirable to enhance thermal contact between thermal sensors 320 and an external wall 111 of shaft 110, particularly if shaft 110 is evacuated to reduce thermal cross-talk errors which might be caused by convection currents within shaft 110. Accordingly, in order to enhance thermal contact between sensors 320 and shaft wall 111, probe 300 provides a mechanism to enhance thermal contact between the sensors 320 and shaft wall 111. A flexible spring-like frame 324 is provided. Frame 324 enhances thermal contact between sensors 320 and shaft wall 111 by pushing sensors 320 firmly against shaft wall 111.

In a recommended method of construction, spring frame 324 is made of a narrow elongated thin strip 361 of flexible metal. Metal strip 361 is cut to fit within an internal lumen 113 of shaft 110. One or more crescent shaped perforations are cut into strip 361, forming tongue-shaped springs 360 which are then bent into such positions that their spring-like actions tend to distance their distal ends from strip 361. In a preferred embodiment thermal sensors 320 are attached to each spring 360. When frame 324, having one or preferably a plurality of tongue-shaped springs 360 each having an attached thermal sensor 320, is introduced into shaft 110 of probe 300, the spring-like action of springs 360 pushes sensors 320 against an external wall 111 of shaft 110, thereby enhancing thermal contact between sensors and wall, and thereby also enhancing thermal contact between sensors 320 and body tissues external to shaft 110 when shaft 110 is inserted in a body.

In an exemplary embodiment presented in FIGS. 3a and 3b, metal frame 234 is constructed of type A metal. Frame 234 thus acts as common thermocouple wire 224, as described hereinabove with respect to an embodiment presented in FIG. 2a. Thermal junctions 320a, 320b and 320N are thus formed by fusing type B metal wires 322a, 322b to 322N to springs 360, as shown in FIG. 3a.

It is noted that various modifications may be introduced without departing from the general scope of the invention. For example, separate wiring (such as presented in FIG. 2b) may be used in place of a 'common-wire' connection through frame 324 shown in FIG. 3a. Other thermal sensors (e.g. thermistors) may be used in place of thermocouples. Crescent shaped springs 360 pointing towards handle 130 rather than towards distal end 115, and may extend in a common direction or in a variety of directions from frame 234. Springs 360 may be in any spring-like shape, and may be attached to frame 234 rather than being cut and bent from a common material. Frame 234 may be constructed as a bent rod forced into shaft 110, with springiness of that bent rod forcing contact between rod and shaft wall.

In a preferred method of construction of probe 300, sensors 320 are thermocouples as discussed with reference to FIGS. 2a and 2b. Frame 234 is prepared by fine machining methods such as laser metal cutting, lithography or electro-erosion, and tongues 360 are bent to form springs. A plurality of springs 360 are formed and a plurality of thermal sensors are attached thereto, preferably by gluing. Connecting wires 322 are aligned with frame 234, which is then carefully placed within shaft 110 Handle 130, with thermal anchor block 232, copper wires 236, cable 132 and connector 134, are then assembled.

Of course, order or detail of steps here listed may be varied without departing from the general scope of the invention. For example, instead of pushing frame 234, with sensors and wires attached, into a probe shaft 110 closed at one end, a long connecting protrusion extending from frame 234 may be used to pull frame 234 into a shaft 110 open at both ends, after which that protrusion may be cut off and a distal end of shaft 110 may then be closed in such a manner as to form sharp point 115.

Figure 3C:
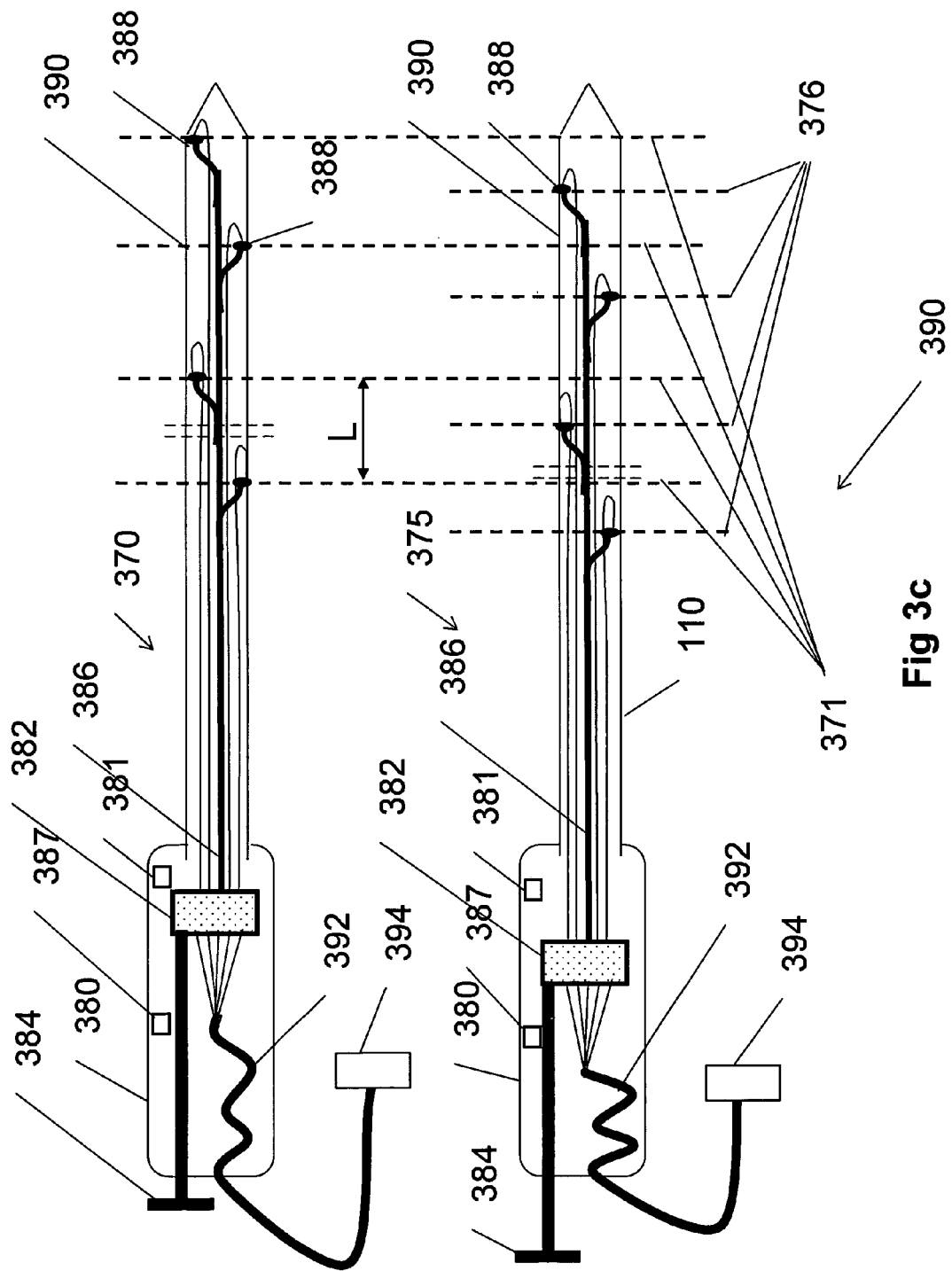
FIG. 3c presents a simplified schematic of a multiple thermal-sensor device with internally moveable sensors, according to an embodiment of the present invention.

Attention is now drawn to FIG. 3c, which presents a multiple thermal-sensor probe 390 which comprises thermal sensors 388 moveable within probe 390, according to an embodiment of the present invention. Probe 390 enables longitudinal translation within a shaft 110 of probe 390 of a frame 386 (similar to frame 234) to which multiple thermal sensors 388 are attached. Probe 390 is advantageous in that it enables finely spaced thermal readings, and further enables modifications in thermal sensor placement, even while probe 390 is immobilized by being embedded in frozen tissue.

Due the necessity to have plurality of connecting wires in the narrow lumen of the shaft 110, there are limitations to the number of sensors capable of being inserted into shaft 110 if shaft 110 is narrow, as is desirable. Yet, in many contexts it is advantageous to be able to make temperature readings with fine resolution along the penetration axis of a thermal probe. Probe 390 enables fine resolution of thermal readings without requiring a large number of thermal sensors.

When a thermal sensor probe is used in non-frozen tissue, it is theoretically possible for that probe to be inserted into tissue at a first depth, be utilized to measure temperature, and then be pulled back or pushed forward to enable temperature reading at another depth. However, such a method of changing sensor probe locations can only be practiced where the probe does not pass through frozen tissue, since freezing of tissue containing a thermal probe will tend to cause the frozen tissue to adhere to the probe, making probe movement impossible or risking tissue damage if the probe is moved by force. Yet use of thermal sensors in contexts involving frozen tissue is typical during cryoablation. Probe 390 solves this problem by enabling sensor movement within probe 390, thereby enabling sensor movement with respect to body tissues even though probe 390 be immobilized within frozen tissues at the time of that movement.

FIG. 3c presents a double side view of probe 390, showing frame 386 with attached sensors 388 in advanced position (view 370) and in retracted position (view 375). For clarity, only essential elements of probe 390 are shown in FIG. 3c. A handle 380 is configured to allow a plunger 384 to push and pull thermal anchor block 382, advancing or retracting block 382 within handle 380. Thermal anchor block 382 is attached to frame 386, consequently frame 386 similarly advances or pulls back within shaft 110 as plunger 384 is pushed and pulled. Flexible cable 392 allows motion of frame 386 while maintaining electrical connection with sensors 388 connected to frame 386, as shown in FIG. 3c. Advanced positions 371 of advanced thermal sensors 388 (shown in view 370) may be contrasted to their retracted positions 376 (shown in view 375) in FIG. 3c.

In a preferred embodiment, sensors 388 are evenly spaced along frame 386, with inter-sensor distance L. If a desired axial resolution is L/M, where M is a small integer number, plunger 384 may be retracted or advanced in step-wise manner, in steps of L/M size, with thermal readings taken at each step. Plunger 384 and frame 386 should then have a range of motion spanning at least L/(M-1).

Range of motion of plunger 384 and frame 386 may be continuous, or may be limited to specifics positional stops. Control of this motion may be manual, or may be mechanized using an actuator 387 powered electrically (e.g. by stepper motor), or hydraulically, or by air pressure, or by other similar means, under automatic (i.e. algorithmic) control.

Plunger 384 may be manufactured as a part of frame 386.

Thermal anchor block 382 may be part of the moveable portion of probe 390 as shown in FIG. 3c, or may be stationary, or absent.

Handle 380 may contain an position sensor 381 for measuring position of frame 386 with respect to shaft 110, and optionally for reporting that location information to data processing unit 460.

Sensor placement of frame 386 may be diffuse or concentrated. In a preferred embodiment, the range of motion of frame 386 exceeds the length of the span of sensors on frame 386.

A wireless handle, as presented hereinabove with respect to FIG. 1b, may be used with any of the abovementioned embodiments.

Attention is now drawn to FIG. 4, which is a simplified schematic of a multiple thermal-sensor apparatus 400 with an interface 410 for communicating with a data processing unit 460, according to an embodiment of the present invention.

Sensing apparatus 400 comprises an interface unit 410 and at least one multiple sensor device 420. Sensor device 420 may be any of the thermal sensor probes discussed hereinabove, or any similar probe. Sensor device 420 connects to interface unit 410 through connector 134 of cable 132. Connector 134 mates with mating connector 434. Preferably, a plurality of sensor devices 420 may be connected to a same sensor interface unit 410.

Sensor interface unit 410 performs signal manipulation on signals received from sensor devices 420, and communicates digital information indicative of measured temperatures to data processing unit 460.

Interface unit 410 may also supply power to sensor devices 420, and may communicate commands serving to control electronics elements within devices 420. For example, if device 420 is a probe 390, sensor interface unit 410 may control actuators used to move frame 386 within probe 390, and may relay information about position of frame 386 within probe 390 to data processing unit 460.

Interface unit 410 may be embodied as an independent unit, or may be housed together with, or be contained by, data processing unit 460. For example, interface unit 410 may be a data acquisition card inserted in a PC computer.

Optionally, connector 134 and mating connector 434 may be absent and interface unit 410 may connect directly to one or more cables 132.

Interface unit 410 is preferably connected to data processing unit 460 via a data cable 414, and uses a proprietary or a standard protocol such as USB, RS232, etc. Alternatively, interface unit 410 may comprise a wireless transmitter 412 for transmitting information to data processing unit 460 using wireless communication means such as infrared, radio frequency communications, or ultrasonic waves. Preferably, wireless communication transmitter 412 is a wireless transceiver allowing two-way communication between interface box 410 and data processing unit 460.

Sensor device 420 may be a wireless probe 150. In this case mating connector 434 may be absent, being replaced by a wireless receiver. Alternatively, wireless probe 150 may communicate directly with data processing unit 460, making interface 410 redundant.

Data processing unit 460 is preferably a digital processor such as a PC, or a DSP unit comprising a processor, a memory for data and program storage, input/output means such as keyboard, a mouse, and other peripherals commonly used with PCs, such as mass data storage devices (hard drive, removable media drive), LAN or Internet communication means, printer, etc.

Optionally, data processing unit 460 is equipped with a display 468 for displaying status of apparatus 400 and for displaying raw and/or processed sensor readings. Data processing unit 460 is operable to calibrate sensor devices 420, to receive raw data transferred therefrom, to perform calculations transforming raw data readings to calculated tissue temperature gradients, and to display that calculated information.

Figure 5:
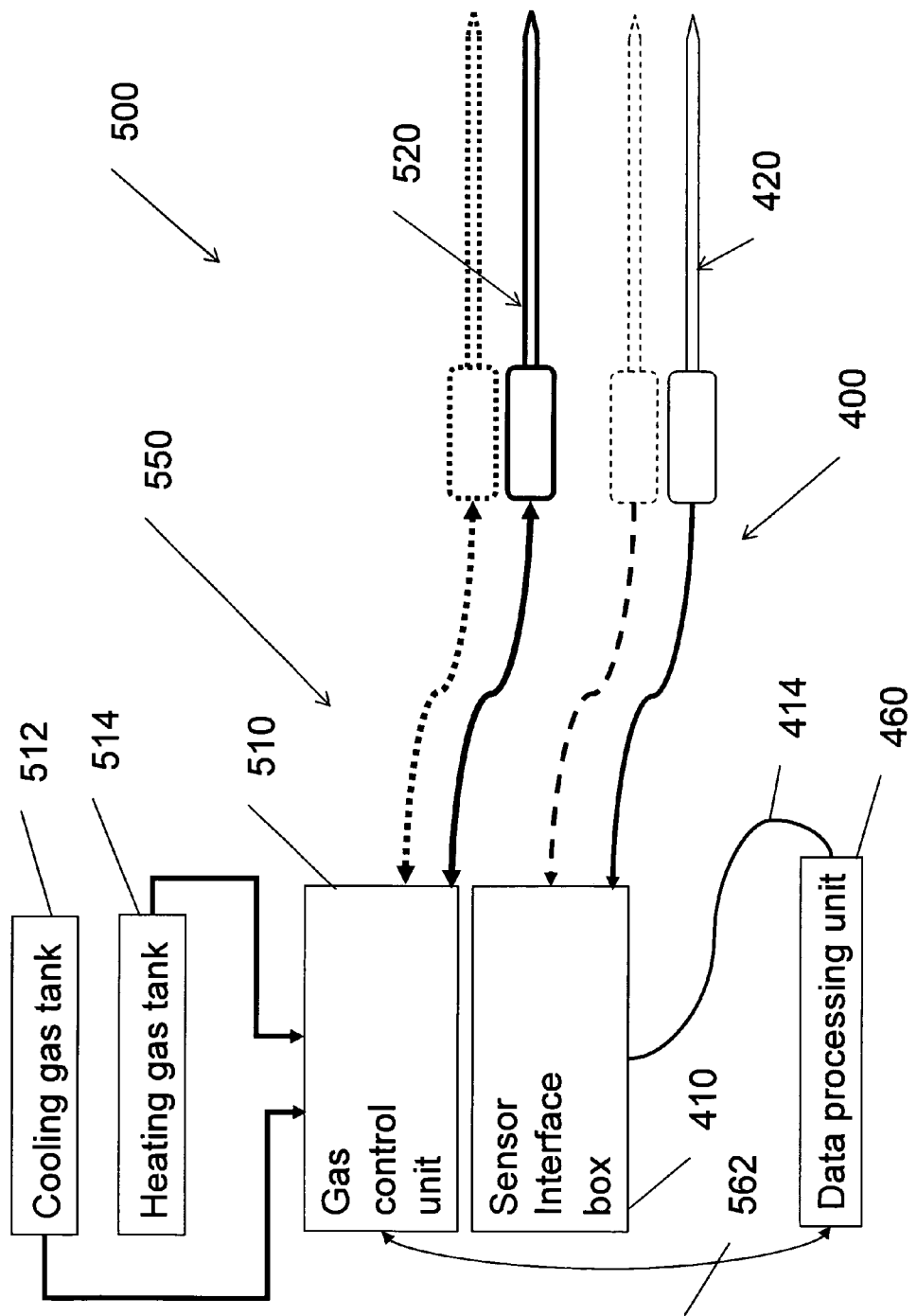
FIG. 5 is a simplified schematic of a cryoablation system using a multiple thermal-sensor device, according to an embodiment of the present invention.

Attention is now drawn to FIG. 5, which is a simplified schematic of a. thermal ablation system 500, according to an embodiment of the present invention. Thermal ablation system 500 incorporates a multiple thermal-sensor apparatus 400, a data processing unit 460, and a thermal ablation apparatus 550.

Sensing apparatus 400 comprises at least one multiple sensor device 420 and a sensor interface unit 410, and is connected to a data processing and control unit 460, optionally via a data cable 414.

Thermal ablation apparatus 550 comprises a thermal control unit 510 operable to receive command signals from data processing unit 460 and to start and/or stop and/or control a thermal ablation process in response to those signals. Data processing unit 460 calculates and originates command signals in response calculations based on temperature readings from multiple sensors 420. Thermal control unit 510 connects to, activates, and controls one or more thermal treatment probes 520, which are capable heating or cooling tissue. Thermal treatment probes 520 may be cryoprobes, in which case thermal control unit 510 controls supply of cryogen to probes 520.

In a preferred embodiment, treatment probes 520 are Joule-Thomson cryoprobes and control unit 510 is operable to supply high pressure cooling gas from tank 512 and high pressure heating gas from tank 514 to one or more probes 520. Data processing unit 460 controls control unit 510, and thus is operable to control thermal activity of probes 520 n response to thermal data collected by sensors 420. Thermal control unit 510 is preferably connected to data processing unit 460 via control cable 562.

During thermal treatment such as cryoablation, information gleaned from a plurality of multiple thermal-sensors probes may be used to provide thermal readings from plurality of locations within a treated area. These readings may be displayed using optional display 468, providing information to the user of apparatus 400 and system 500. Optionally, thermal readings from a plurality of multiple thermal-sensor devices may be used to create a three-dimensional model of temperature distribution within a treated area, which model may be displayed to a user and/or may be used as a basis for calculating operational parameters used to govern an automated treatment process, e.g. by generating and sending commands to gas control unit 510.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A thermal sensor probe comprising a distal portion insertable into a body, said distal portion comprises:
   a) a hollow portion;
   b) a sealed external wall separating all parts of said hollow from contact with body tissues and body fluids external to said wall when said distal portion is inserted in a body; and
   c) at least one thermal sensor positioned within said hollow and operable to report temperature information dependent on temperature of tissues adjacent to said distal portion when said distal portion is inserted in a body; and
   d) a mechanism for moving said sensor within said hollow while said distal portion is inserted in a body.

2. The probe of claim 1, further comprising a plurality of said thermal sensors.

3. The probe of claim 1, wherein said thermal sensor is selected from a group consisting of a thermocouple and a thermistor.

4. The probe of claim 1, wherein said thermal sensor is operable to be moved within said probe by a mechanical actuator under algorithmic control.

5. The probe of claim 1, further comprising a position sensor operable to sense and report a position of said thermal sensor within said probe.

6. The probe of claim 1, wherein said thermal sensor is mounted on a frame and said frame is moveable within said hollow.

7. The probe of claim 6, further comprising a plurality of thermal sensors mounted on said frame.

8. The probe of claim 7, further comprising thermal isolation between individual sensors of said plurality of sensors.

9. The probe of claim 7, wherein said plurality of thermal sensors are mounted on springy portions of said frame, and at least one of said springy portions is so shaped and so positioned that a thermal sensor mounted thereon is pushed into close contact with said external wall when said frame is positioned within said hollow.

10. A thermal sensor probe insertable into body tissue comprising
   a shaft comprising a hollow and a frame inserted therein;
   a plurality of thermal sensors distributed along said shaft,
      wherein at least one of said plurality of thermal sensors is mounted on a spring attached to said frame and held with pressure against an internal portion of an external wall of said shaft when said frame is inserted in said shaft and wherein each of said sensors being so positioned as to be in direct contact with a portion of said shaft and operable to measure temperature of tissues external to said shaft when said shaft is inserted in a body of a patient; and
   a mechanism for moving said frame within said probe.

11. The probe of claim 10, wherein at least one of said thermal sensors is mounted on an external portion of said shaft and covered by a biocompatible coating.

12. The probe of claim 10, wherein said hollow is sealed so as to prevent all contact between contents of said hollow and body tissues and body fluids external to said shaft when said shaft is inserted in said body.

13. The probe of claim 10, wherein at least one of said sensors is a thermocouple.

14. The probe of claim 10, wherein at least one of said sensors is a thermistor.

15. The probe of claim 10, further comprising a first electronic element operable to receive and process a first signal from one of said thermal sensors and a second electronic element operable to transmit a second signal to a remote data processing unit.

16. The probe of claim 15, wherein said second electronic element is a wireless transmitter.

17. The probe of claim 15, wherein said first and second electronic elements are positioned in a handle of said probe.

18. The probe of claim 10, wherein said plurality of sensors are so positioned that a minimum distance between one and another of said plurality of sensors is at least an order of magnitude greater than a maximum thickness of said external wall of at least that portion of said shaft inserted in said body.

19. A thermal sensor probe insertable into body tissue comprising a hollow shaft and at least one thermal sensor, wherein said thermal sensor is mounted on a spring attached to a frame and is pushed against an internal portion of an external wall of said shaft when said frame is inserted in said shaft, and said thermal sensor is operable to report a temperature reading related to temperature of tissue external to said external wall when said thermal sensor is so positioned.

20. The probe of claim 19, further comprising a plurality of said thermal sensors mounted on a plurality of springs attached to said frame.

21. The probe of claim 19, wherein said thermal sensor is a thermocouple.

22. The probe of claim 19, wherein said thermal sensor is a thermistor.

23. The probe of claim 19, wherein said frame is operable to be moveable within said shaft when said probe is inserted in a body.

24. The probe of claim 19, wherein said shaft comprises at least a partial vacuum.

25. The probe of claim 21, wherein at least one of said thermal sensors is a thermocouple which comprises two different metals, and one of said metals is comprised in said frame.

26. The probe of claim 10, further comprising at least one sub-divider serving to restrict movement of gas between a first vicinity of a first of said plurality of thermal sensors and a second vicinity of a second of said plurality of thermal sensors.

27. The probe of claim 26 further comprising a plurality of sub-dividers each serving to restrict movement of gas from a vicinity of one of said plurality of thermal sensors to a vicinity of another of said plurality of thermal sensors.

28. The probe of claim 26, wherein said sub-divider comprises a glue-like substance deposited within a hollow shaft of said probe.

29. The probe of claim 19, wherein all portions of said hollow of said shaft are sealed from contact with body tissues external to said shaft when said shaft is inserted in a body.

30. A method of constructing a thermal sensor probe, comprising:
  (a) providing a shaft sized to be insertable in a body, said shaft comprises a hollow sealed at its distal end;
  (b) providing a frame which comprises a plurality of springy elements;
  (c) mounting a plurality of thermal sensors on said frame, each sensor on a one of said springy elements; and
  (d) inserting said frame with said plurality of mounted thermal sensors into said hollow so that at least one of said springy elements presses at least one of said thermal sensors against an interior portion of an exterior wall of said hollow shaft.

31. A probe which comprises:
  a) a shaft comprising a hollow and a distal portion insertable into a body;
  b) a thermal sensor mechanism comprising a plurality of thermal sensors, wherein at least one of said plurality of thermal sensors is mounted on a spring attached to a frame and held with pressure against an internal portion of an external wall of said shaft when said frame is inserted and moved within said hollow of said shaft, and wherein said thermal sensor mechanism is operable to detect whether body tissues adjacent to all inserted portions of said probe are at a temperature above freezing; and
  c) a visible indicator designed to provide a status indication indicating whether said sensor mechanism detects above-freezing temperatures along all inserted portions of said probe.

32. The probe of claim 31, wherein said plurality of thermal sensors are in said distal portion.

33. The probe of claim 31, wherein a status indicated by said indicator is visible from a distance of at least a meter.

34. The probe of claim 31, further comprising a cooling mechanism operable to cool a portion of said probe to below-freezing temperatures.

* * * * *